(12) United States Patent
Biedermann et al.

(10) Patent No.: US 8,998,965 B2
(45) Date of Patent: *Apr. 7, 2015

(54) BONE ANCHORING DEVICE

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/005,285

(22) Filed: Jan. 12, 2011

(65) Prior Publication Data

US 2011/0112585 A1 May 12, 2011

Related U.S. Application Data

(63) Continuation of application No. 11/934,625, filed on Nov. 2, 2007, now Pat. No. 7,892,259.

(60) Provisional application No. 60/859,642, filed on Nov. 17, 2006.

(30) Foreign Application Priority Data

Nov. 17, 2006 (EP) ..................................... 06023910

(51) Int. Cl.
*A61B 17/86* (2006.01)
*A61B 17/88* (2006.01)
*A61B 17/70* (2006.01)

(52) U.S. Cl.
CPC ....... *A61B 17/7038* (2013.01); *Y10T 29/49826* (2015.01); *A61B 17/7032* (2013.01); *A61B 17/7037* (2013.01)

(58) Field of Classification Search
CPC .................................................. A61B 17/7038
USPC ......... 606/264–270, 272, 279, 305–308, 319, 606/328
See application file for complete search history.

(56) References Cited

U.S. PATENT DOCUMENTS 5,499,983 A * 3/1996 Hughes .......................... 606/267
5,752,957 A * 5/1998 Ralph et al. .................... 606/266
(Continued)

FOREIGN PATENT DOCUMENTS

DE 10005386 A1 8/2001
EP 0879579 A2 11/1998
(Continued)

OTHER PUBLICATIONS

European Search Report dated Apr. 19, 2007 for EPO Application No. EP 06023910.0, European Search Report mailed May 2, 2007. Biedermann Motech GmbH (7 pp.).

*Primary Examiner* — Eduardo C Robert
*Assistant Examiner* — Jacqueline Johanas
(74) *Attorney, Agent, or Firm* — Christie, Parker & Hale, LLP

(57) ABSTRACT

A bone anchoring device includes a receiving part for receiving a rod, the receiving part having a first bore coaxial with a longitudinal axis and a second bore. The bone anchoring device also includes an anchoring element having a first end for insertion into the bone and a second end positionable within a second bore, the second end having a spherically shaped surface portion. The bone anchoring device further has a locking device provided to the second bore of the receiving part. The locking device protrudes from an inner wall of the second bore and engages with a recessed surface portion of the second end of the anchoring element, such that the anchoring element is pivotable relative to the receiving part around a single axis of rotation. The locking device may comprise pins inserted into through holes formed in the receiving part, which engage with the recessed surface portion of the second end.

10 Claims, 9 Drawing Sheets

(56) References Cited

U.S. PATENT DOCUMENTS

| | | | |
|---|---|---|---|
| 5,989,254 A * | 11/1999 | Katz | 606/308 |
| 6,368,321 B1 * | 4/2002 | Jackson | 606/270 |
| 7,850,718 B2 * | 12/2010 | Bette et al. | 606/267 |
| 7,951,172 B2 * | 5/2011 | Chao et al. | 606/265 |
| 8,038,701 B2 * | 10/2011 | Rock et al. | 606/266 |
| 8,419,778 B2 * | 4/2013 | Barry | 606/308 |
| 8,603,145 B2 * | 12/2013 | Forton et al. | 606/272 |
| 8,636,783 B2 * | 1/2014 | Crall et al. | 606/308 |
| 2002/0173789 A1 * | 11/2002 | Howland | 606/61 |
| 2003/0187439 A1 | 10/2003 | Biedermann et al. | |
| 2004/0186474 A1 | 9/2004 | Matthis et al. | |
| 2004/0204711 A1 * | 10/2004 | Jackson | 606/61 |
| 2005/0261687 A1 * | 11/2005 | Garamszegi et al. | 606/61 |
| 2006/0089644 A1 | 4/2006 | Felix | |
| 2006/0111715 A1 * | 5/2006 | Jackson | 606/61 |
| 2006/0155277 A1 | 7/2006 | Metz-Stavenhagen | |
| 2006/0200131 A1 | 9/2006 | Chao et al. | |
| 2007/0043355 A1 * | 2/2007 | Bette et al. | 606/61 |
| 2007/0088357 A1 * | 4/2007 | Johnson et al. | 606/61 |
| 2007/0090238 A1 * | 4/2007 | Justis | 248/181.1 |
| 2008/0177322 A1 * | 7/2008 | Davis et al. | 606/266 |
| 2008/0183223 A1 * | 7/2008 | Jeon et al. | 606/305 |
| 2008/0195159 A1 | 8/2008 | Kloss et al. | |
| 2008/0234759 A1 * | 9/2008 | Marino | 606/309 |
| 2008/0288002 A1 * | 11/2008 | Crall et al. | 606/308 |
| 2009/0076552 A1 * | 3/2009 | Tornier | 606/264 |
| 2009/0105769 A1 * | 4/2009 | Rock et al. | 606/308 |
| 2010/0152785 A1 * | 6/2010 | Forton et al. | 606/301 |
| 2011/0106175 A1 * | 5/2011 | Rezach | 606/305 |
| 2011/0178558 A1 * | 7/2011 | Barry | 606/302 |
| 2011/0178559 A1 * | 7/2011 | Barry | 606/302 |
| 2011/0257690 A1 * | 10/2011 | Rezach | 606/302 |

FOREIGN PATENT DOCUMENTS

| | | |
|---|---|---|
| KR | 2003-0078008 A | 10/2003 |
| KR | 10-2005-0080493 | 8/2005 |
| WO | WO 2005/074823 A1 | 8/2005 |
| WO | WO 2006/084443 A1 | 8/2006 |
| WO | WO 2006/096306 A2 | 9/2006 |

* cited by examiner

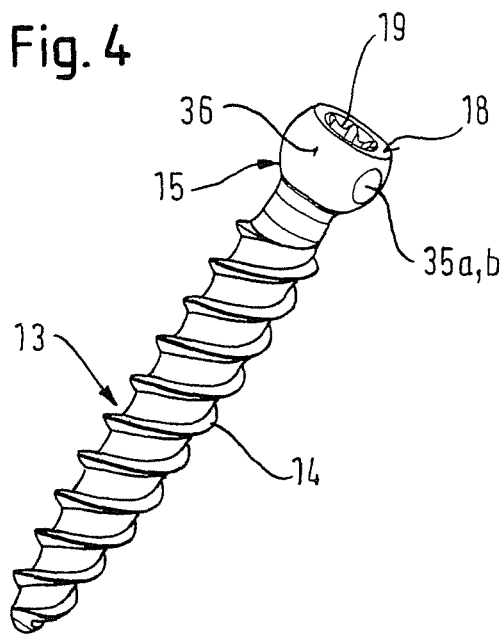
Fig. 4
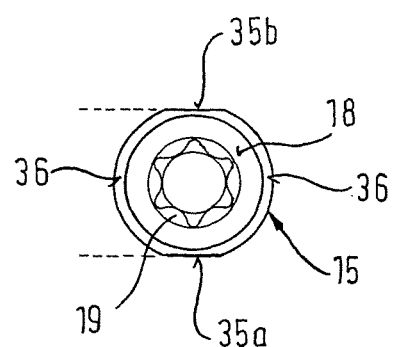
Fig. 5
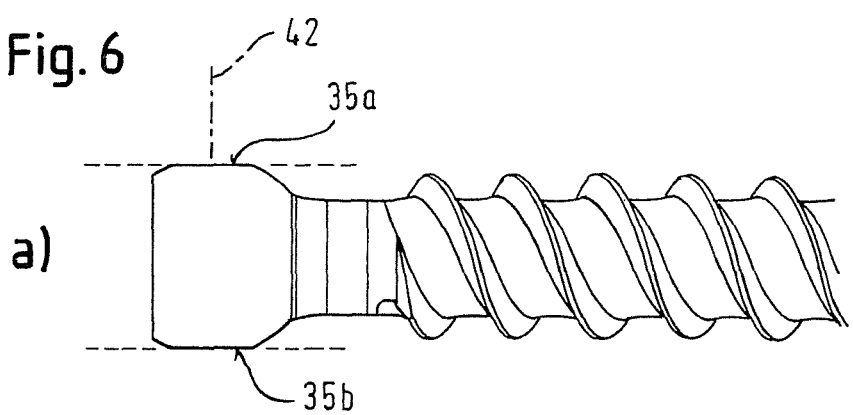
Fig. 6
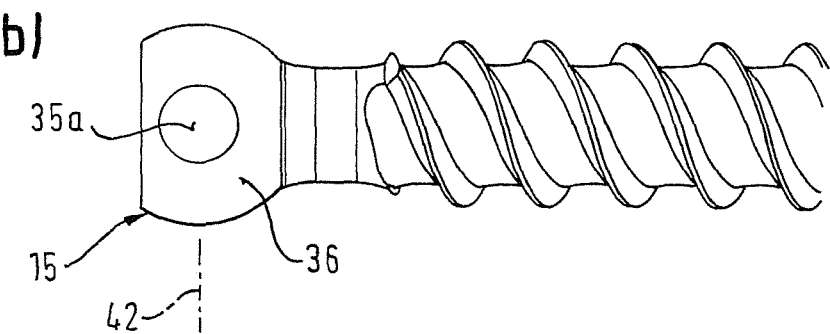

Fig. 10
a)
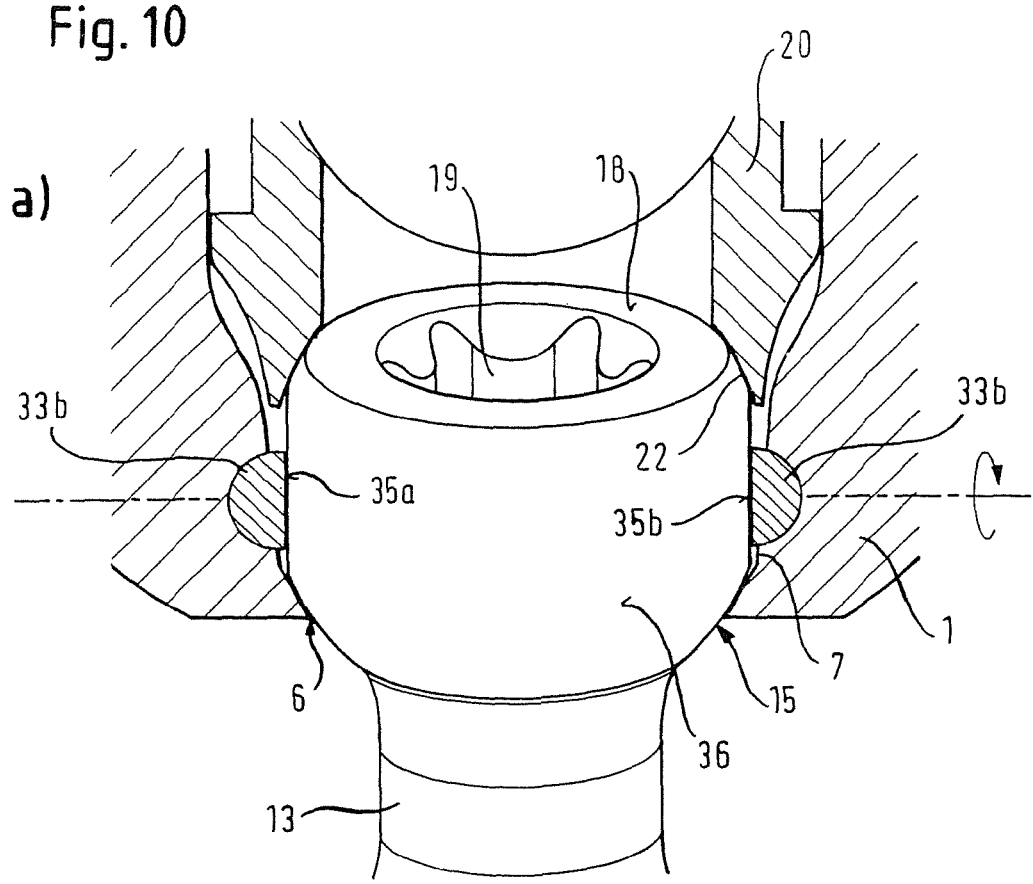
b)
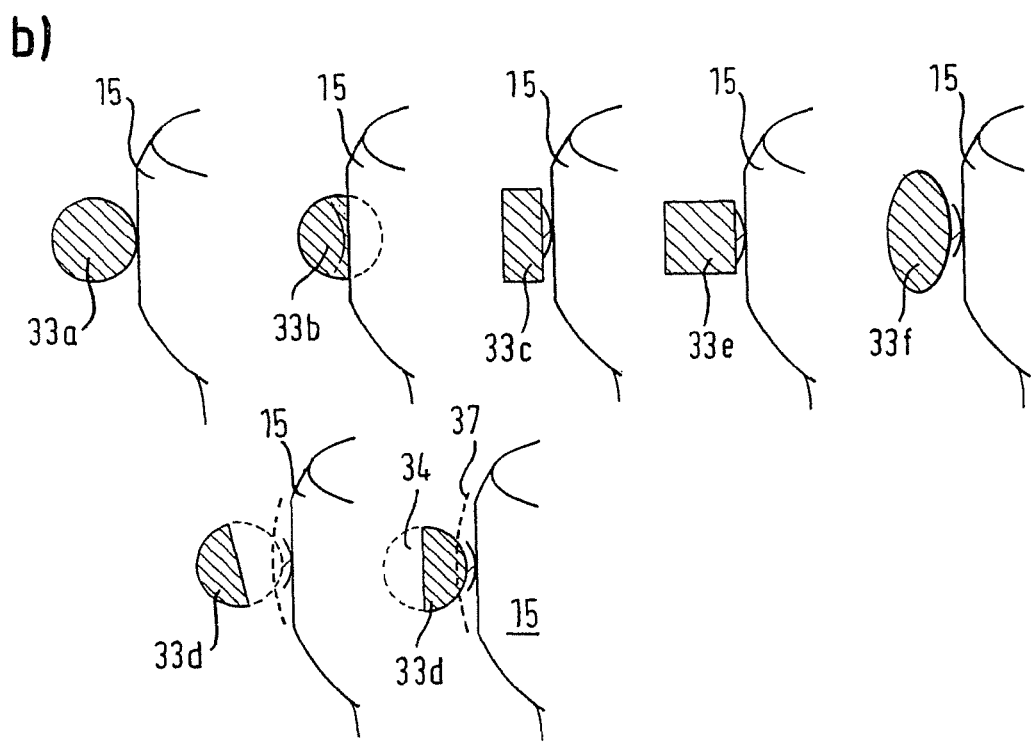

Fig. 11
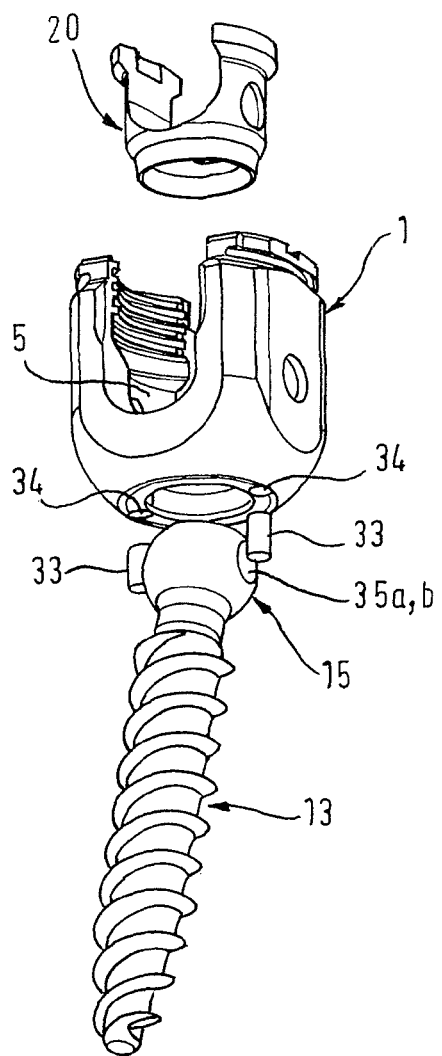
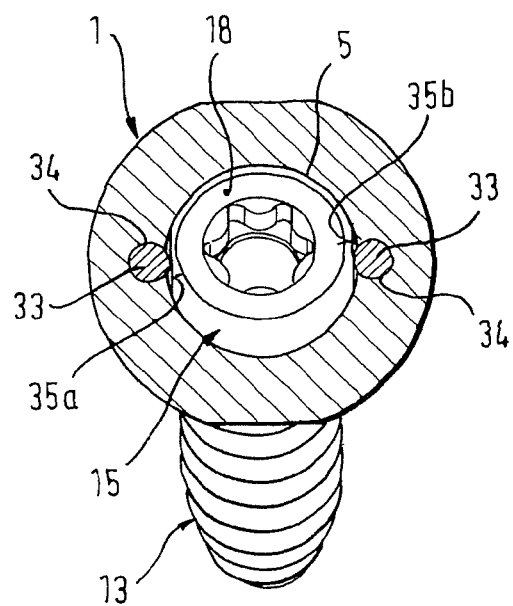

Fig. 12
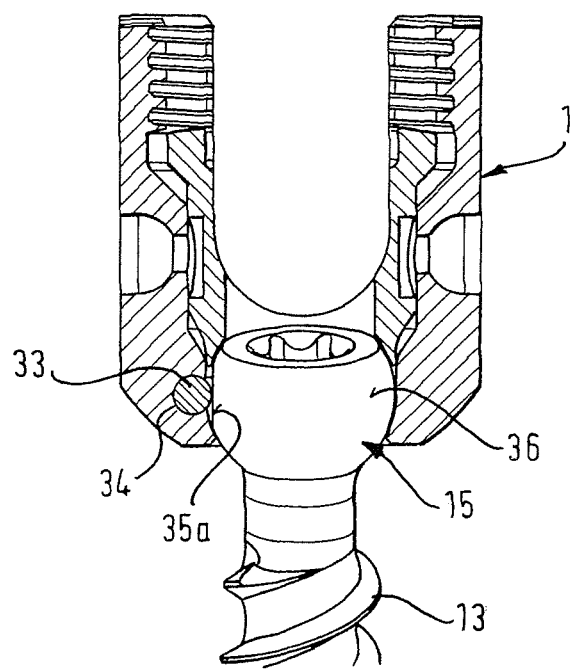
a)
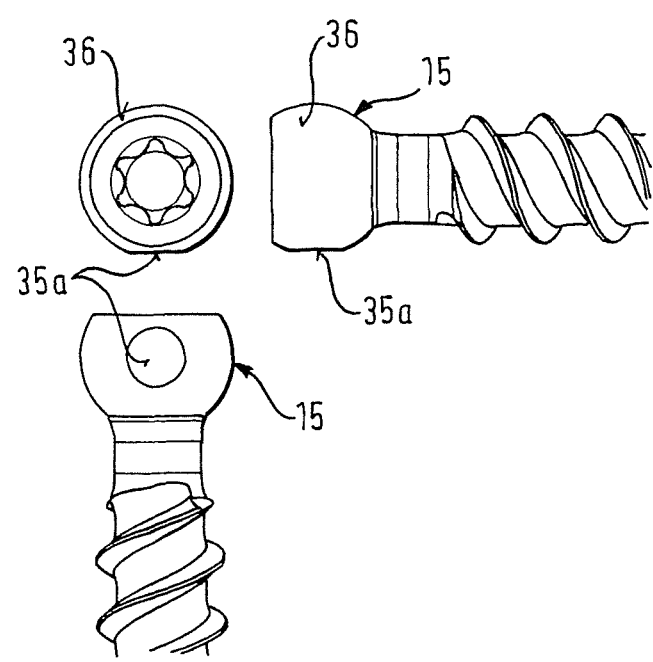
b)

BONE ANCHORING DEVICE

CROSS-REFERENCE TO RELATED APPLICATION(S)

This application is a continuation of U.S. patent application Ser. No. 11/934,625, filed Nov. 2, 2007, now U.S. Pat. No. 7,892,259 which claims priority to and the benefit of U.S. Provisional Patent Application No. 60/859,642, filed Nov. 17, 2006, and claims priority from European Patent Application EP 06023910.0, filed Nov. 17, 2006, the disclosures of which are incorporated herein by reference.

BACKGROUND

The invention relates to a bone anchoring device which comprises a receiving part for receiving a rod, an anchoring element having a first end for insertion into the bone and a second end held in the receiving part, and a locking device to limit a pivoting movement of the anchoring element to pivoting around a single axis.

Document US 2006/0155277 A1 discloses an anchoring element, which comprises a retaining means for receiving a rod, the retaining means having a ring-shaped mount, a fastening element for anchoring the device in the vertebra, and a securing element which can be screwed into a thread of the retaining means in order to fix the fastening element with an angle relative to the retaining means.

The fastening element comprises a threaded shank and a bearing, the latter being provided to achieve a pivotal motion when being supported by a separate intermediate element, which can be inserted into the ring-shaped mount of the retaining means. More specifically, the bearing includes spherical surfaces which engage with spherical counterparts of the intermediate element. The bearing further has two flat guiding surfaces formed on opposite sides thereof, which engage with respectively flat counter surfaces of the intermediate element.

The fastening element may perform a rotation movement around one single axis with respect to the intermediate element. However, the intermediate element can freely rotate within the mount around a longitudinal axis of the retaining means. Hence, a polyaxial adjustment of the fastening element relative to the retaining means is possible.

The final fixation is achieved by screwing the securing element into the thread of the retaining means after the rod is inserted. As a result thereof, pressure is exerted onto the rod, which transmits this pressure further to the intermediate element which then frictionally clamps the bearing. Thus, upon fixation by the securing element, the degree of free movement is reduced from polyaxial to fully rigid at the same time.

For certain applications it is desirable to have a bone anchoring device which allows an adjustment of the angle between the bone anchoring element and the receiving part in one single plane.

Based on the foregoing, there is a need for a bone anchoring device, which simplifies handling of an anchoring device and increases its stability against external forces once the device has been fixated using a fixation element.

SUMMARY

The present bone anchoring device is arranged to reduce rotation of the anchoring element to rotation around one single axis prior to fixation. For this purpose, a locking device is provided at an inner wall of the receiving part which engages with the surface of the head of the anchoring element in order to impede rotation of the anchoring element around, e.g., a longitudinal axis of the receiving part. The locking device and the engaging surface are constructed such as to allow pivotal motion around one single axis, which in this example may be oriented perpendicular to the longitudinal axis.

As a result, there is only one axis of rotation upon installation of the anchoring devices and the rod. The handling during installation may thus be simplified. Limiting the pivotal movement of the anchoring devices with regard to the receiving part to just one single axis serves to simplify the handling of the parts of the anchoring device during application to the bones and increases the stability of the installed parts with respect to external forces.

Further features and advantages of the bone anchoring device will become apparent and will be best understood by reference of the following detailed description taken in conjunction with the accompanying drawings.

BRIEF DESCRIPTION OF THE DRAWINGS

FIG. 4 shows a perspective view of an anchoring element;

FIG. 5 shows a top view of a head of the anchoring element shown in FIG. 4;

FIG. 6*a* shows a side view of the anchoring element shown in FIG. 4 with flat guiding surface portions seen in profile;

FIG. 6*b* shows a side view of the anchoring element shown in FIG. 6*a*, but with flat guiding surface portions oriented towards observer (90 degrees rotated);

FIGS. 10*a, b* show alternative embodiments of pins;

FIGS. 11*a, b* show an embodiment wherein the through holes are arranged in a longitudinal direction with respect to the receiving part;

FIGS. 12*a, b* show an embodiment wherein only one through hole is formed in the receiving part, with FIG. 12*a* showing an exploded view, whereas FIG. 12*b* shows a cross-sectional profile in a horizontal plane with respect to the receiving part.

DETAILED DESCRIPTION

Figure 1:
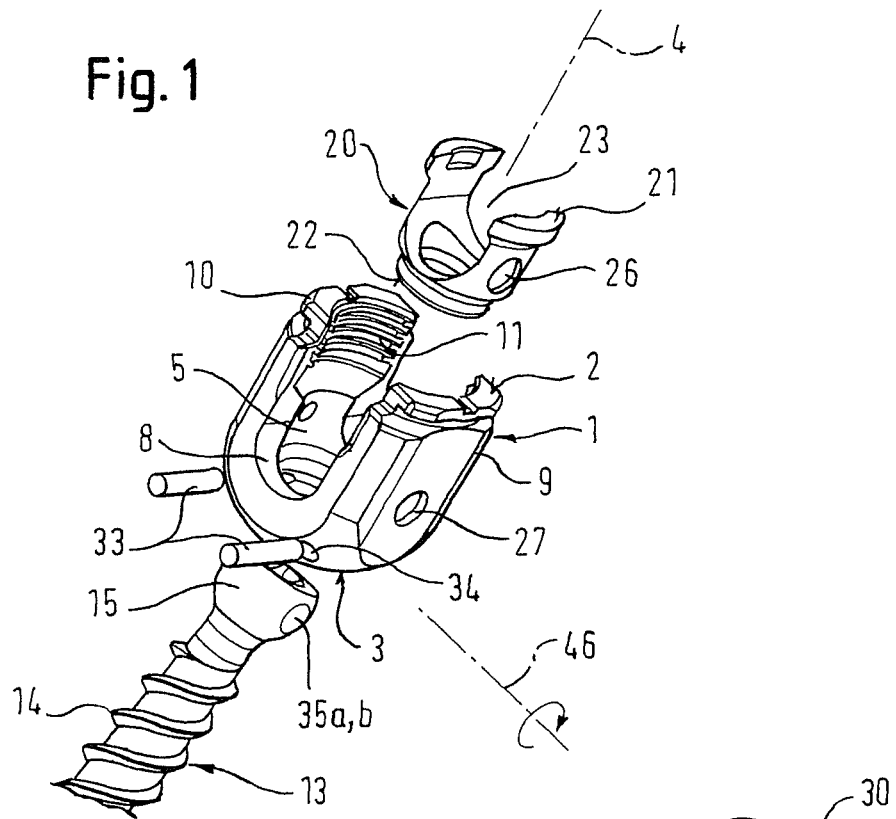
FIG. 1 shows a perspective exploded view of a bone anchoring device according to an embodiment prior to assembly.
Figure 2:
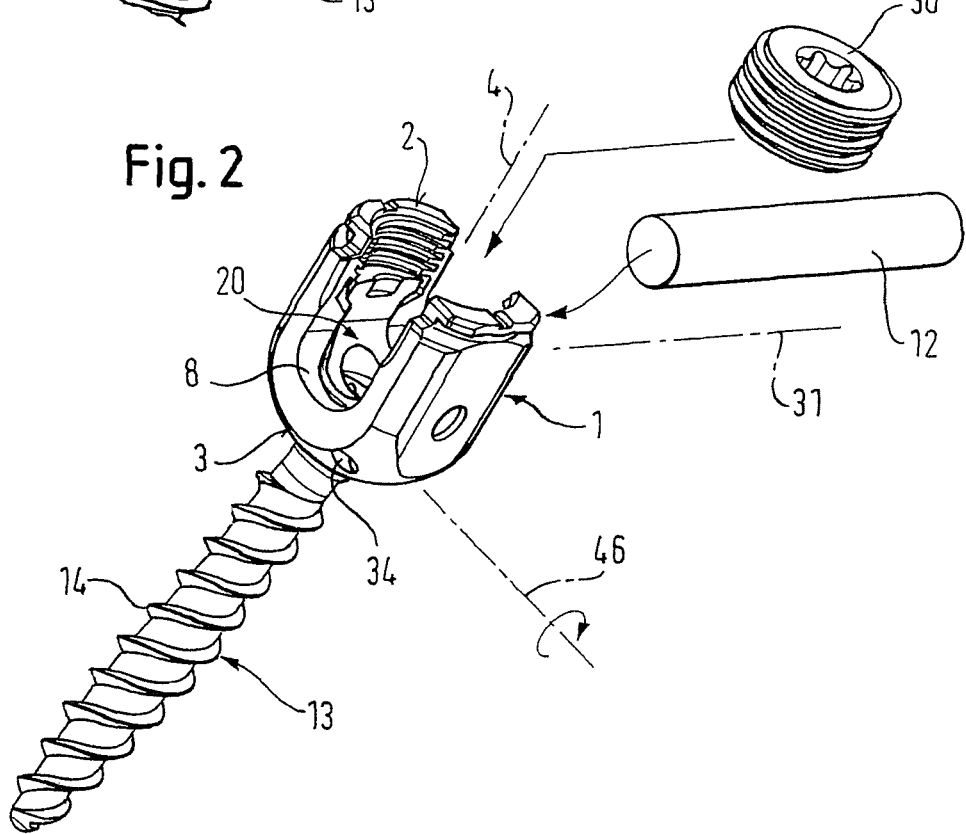
FIG. 2 shows a perspective exploded view of the bone anchoring device according to FIG. 1, but after partial assembly.
Figure 3:
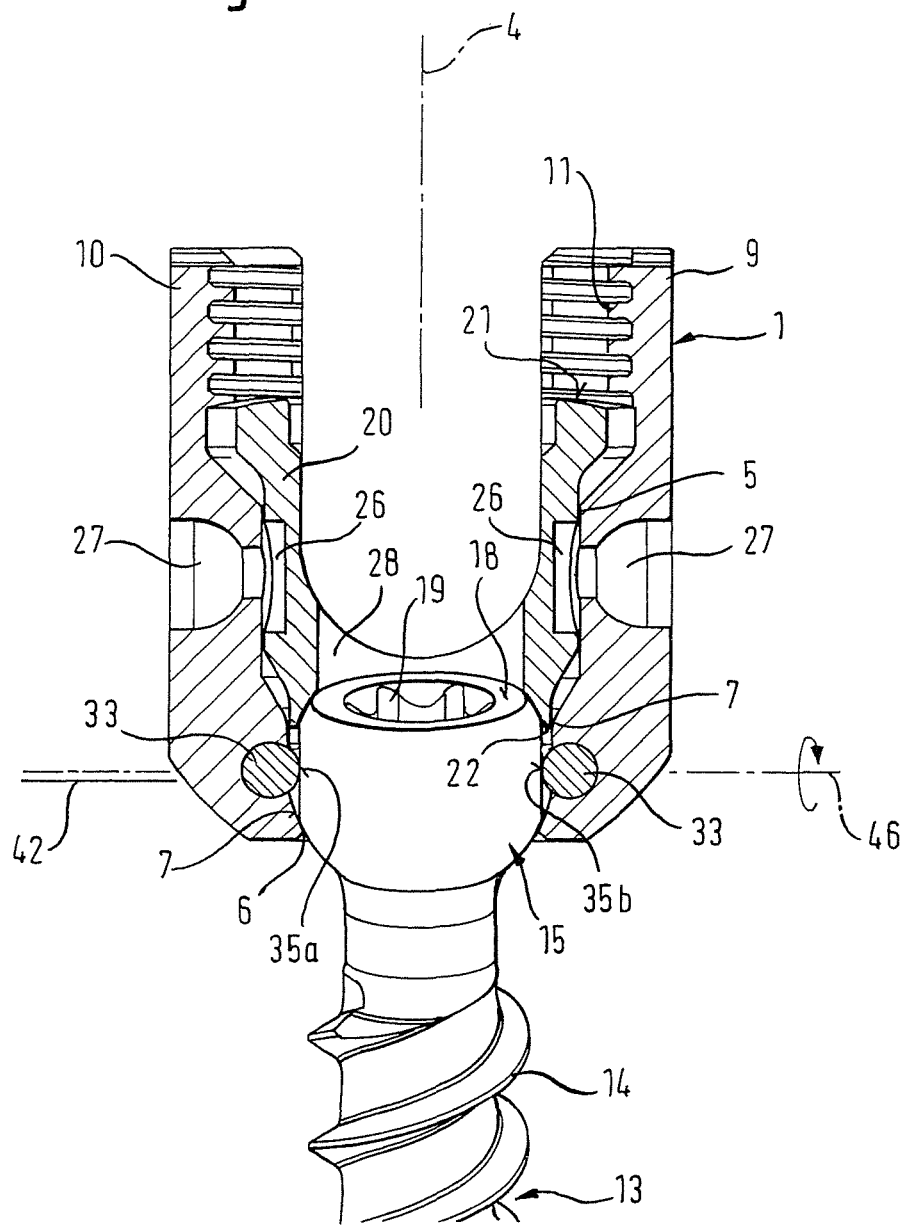
FIG. 3 shows a partial sectional view of the bone anchoring device according to the partially assembled state of FIG. 2, with a sectional plane defined by a longitudinal axis and a pivotal axis.

FIGS. 1 to 3 show in a perspective view a first embodiment of a bone anchoring device, wherein FIG. 1 reveals a situation prior to assembly, FIG. 2 shows details after assembly, and FIG. 3 shows a partly cross sectional profile of the embodiment illustrated in FIGS. 1 and 2 without rod and fixation element.

The bone anchoring device includes a receiving part 1 which has a first end 2 and a second end 3 opposite to the first end. The two ends extend perpendicular to a longitudinal axis 4. Coaxially formed with the longitudinal axis 4, a bore 5 is provided which extends from the first end 2 to a predetermined distance from the second end 3. At the second end 3 an opening or second bore 6 is provided, the diameter of which is smaller than the diameter of the bore 5. The coaxial bore 5 tapers towards the opening 6 in a section 7 which can be for example spherically, conically or otherwise shaped.

The receiving part 1 further has a substantially U-shaped recess 8 which starts from the first end 2 and extends in the direction of the second end 3 to a predetermined distance from said second end 3. By means of the U-shaped recess 8 two free legs 9, 10 are formed extending towards the first end 2.

Adjacent to the first end 2, the receiving part 1 includes an internal thread 11 on said legs 9, 10. The U-shaped recess 8 serves for receiving a rod 12 by which several bone anchoring devices can be connected. A screw 30 cooperating with the internal thread is used as a fixation element. The U-shaped recess 8 further defines an axis 31 along which the rod 12 is oriented upon installation in the U-shaped recess 8. In this specific embodiment, axis 31 is perpendicular to the longitudinal axis 4.

The bone anchoring device further has a bone anchoring element 13 which includes a shank 14 with a bone thread and a head 15 at one end. It is noted that the shank 14 of the anchoring element 13 may not necessarily be threaded and may include other forms suited to apply the anchoring device.

As shown in more detail in FIGS. 4 to 6, the head 15 has a spherical surface portion 16 with the center M (not shown) of a respective sphere 36 lying in the center of the head 15. The head 15 further has two substantially flat surface portions 35a, 35b recessed from an ideal sphere as defined by spherical surface portion 16. The flat surface portions are positioned on opposite sides of the head 15 and are oriented parallel to each other.

On the side opposite to the shank 14, the head 15 may include a flat surface 18. A recess 19 for engagement with a screwing-in tool can be provided in the flat surface 18. The head 15 rests in the section 7 of the receiving part 1 which thus forms a seat for the head 15.

A pressure element 20 is provided for acting onto the head 15. The pressure element 20 is substantially cylindrically-shaped and comprises a first end 21 and a second end 22. The outer diameter of the pressure element 20 is slightly smaller than the inner diameter of the bore 5 of the receiving part 1 so that the pressure element 20 can be inserted into the receiving part 1 and can slide within the bore 5. Adjacent to the first end 21 the pressure element 20 comprises a cylindrical segment-shaped recess 23, the size of which is such that the rod 12 fits in the recess 23.

Adjacent to the second end 22 the pressure element 20 includes a spherically shaped inner surface. The radius of the sphere corresponds to that of the head 15. The pressure element 20 further has a coaxial bore 28 for allowing access for a screwing in tool to the recess 19 in the head 15. The pressure element 20 can further be secured against falling out of the receiving part 1 once it has been inserted, or against rotation within the receiving part 1, for example by means of crimp bores 27 or means exerting a similar function. However, the bone anchoring device is not limited thereto.

Figure 8:
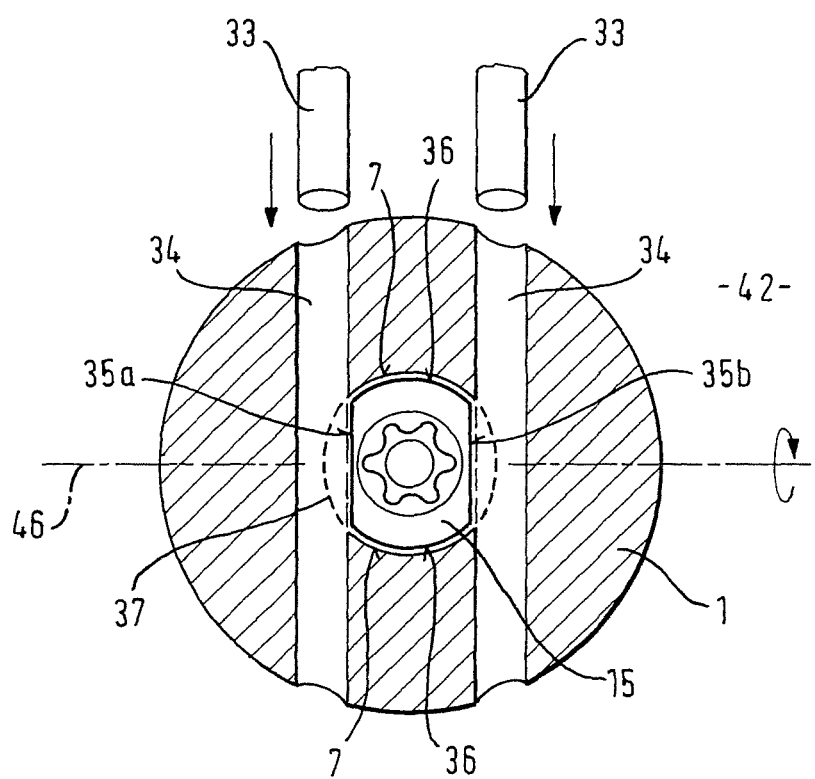
FIG. 8 shows the arrangement of through holes in a cross-sectional profile through a horizontal plane labeled as 42 in FIG. 3, the plane containing the rotational axis.

The receiving part 1 according to this embodiment further includes two through holes 34 each receiving a pin 33. The diameter of the pins 33 corresponds to that of the through holes 34. The through holes 34 are located on opposite sides in the region of the seat 7 and traverse the body of receiving part 1. The through holes 34 also traverse an inner space as defined by the seat 7 of the receiving part 1, which becomes visible from a cross-sectional profile of a plane perpendicular to the longitudinal axis 4 as shown in FIG. 8. More specifically, the through holes 34 are open towards the inner wall of the seat 7 of the receiving part 1. Consequently, the diameter of the space defined by the seat 7 is reduced, when pins 33 are inserted into the through holes 34. In other words the pins 33 protrude from the inner surface of the seat 7 when residing within the through holes 34.

Once being inserted into the through holes 34 of the body of the receiving part 1, the pins 33 engage with the flat surface portions 35a, 35b of the head 15 of the anchoring element 13. As a result thereof, the head 15 cannot be rotated within a plane perpendicular to the longitudinal axis 4 due to the presence of the pins 33, as it is illustrated in FIG. 8. However, as the flat surfaces 35a, 35b serve as guiding surfaces, a pivotal motion around a rotation axis 46 as shown in FIG. 2 is retained.

In this embodiment, the U-shaped recess 8 is aligned with the direction of the through holes 34, such that the rotation axis 46 is perpendicular to the longitudinal axis 4 and to the rod axis 31. Accordingly, rotation of the anchoring element 13 is enabled in a plane defined by the longitudinal axis 4 and the axis 31 (see FIG. 2). It is noted, however, that it is also within the scope of the invention to orient the through holes (and thus the pins upon insertion) perpendicular to the rod axis. Rotation is then enabled in a plane perpendicular to the rod direction.

Figure 9:
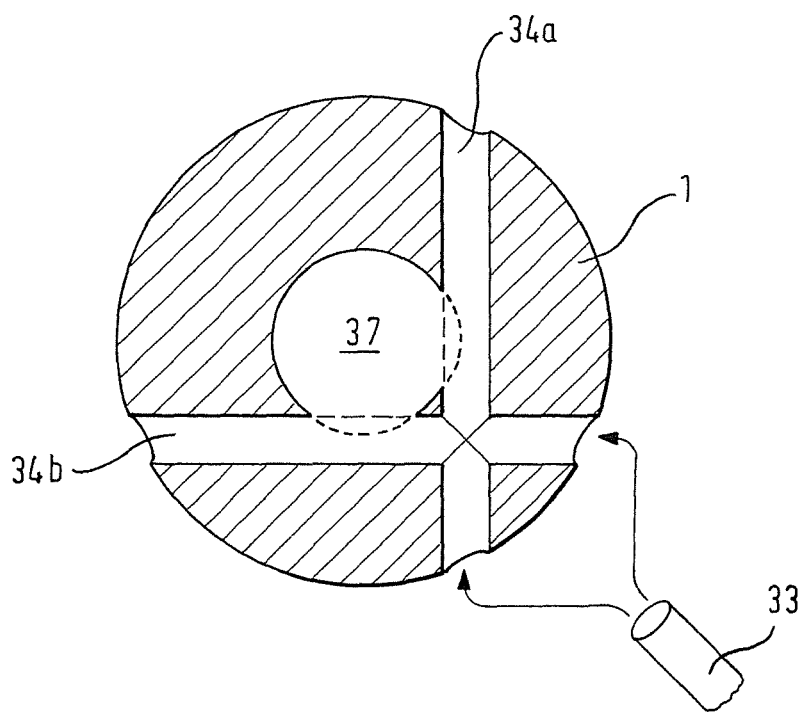
FIG. 9 shows an alternative embodiment of an arrangement of through holes.

It becomes clear to the person skilled in the art, that any direction of the through holes 34 as formed in the receiving part 1 may be constructed according the specific needs. FIG. 9 shows another embodiment, wherein multiple through holes 34a, 34b are formed perpendicular to and cross each other. The pin may be inserted either into through hole 34a, or alternatively into through hole 34b. Only one through hole 34a, 34b per direction is shown. Using the bone anchoring device according to this embodiment, the surgeon may in-situ decide which rotational axis is presently preferred to achieve stability.

Figure 7:
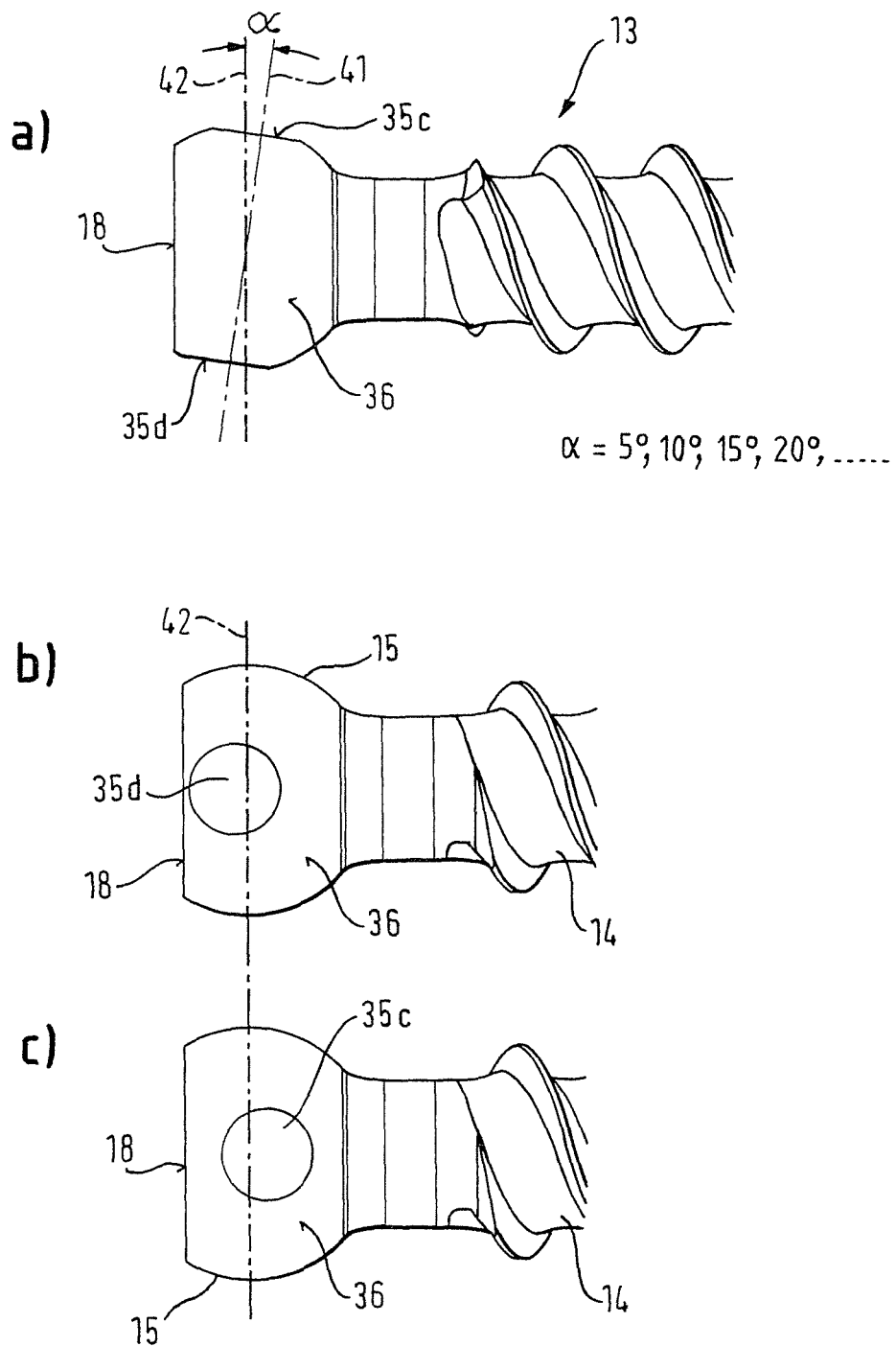
FIGS. 7*a-c* show an alternative embodiment of a head with flat guiding surfaces being inclined with respect to an axis of the shank of the anchoring element.

According to a further embodiment illustrated in FIGS. 7a-c, the orientation of the surface normal 41 of the flat guiding surfaces 35c, 35d is inclined with respect to a plane defined by the top surface 18 of the anchoring element 13. As a result inclined angles α of the threaded shafts 14 with respect to the longitudinal axis 4 of the receiving part 1 may be accomplished. A set of anchoring elements with different inclination angles α=0°, 5°, 10°, 15°, etc., respectively, may be supplied for example, from which the surgeon may choose according to the situation. It is noted that the rotation axis 46 is retained in this embodiment.

It is noted that the whole device including the pins is preferably made of a biocompatible material, for example titanium, titanium alloy or stainless steel, etc.

The bone anchoring device described in the present embodiments may be assembled upon the instance of actually carrying out surgery. However, the device may as well be preassembled. In such a preassembled condition, the anchoring element is screwed into the bone.

In the specific embodiments detailed herein pivoting within a single plane is accomplished by means of the pins 33 acting onto the flat guiding surfaces 35a-d of head 15, which allows pivoting around rotation axis 46, but prevents pivoting around other axes 4, 31. Therefore, an adjustment of the position of the receiving part 1 with respect to the anchoring element 13 within a plane that includes the rod axis is possible, whereas an adjustment in a direction perpendicular to the rod axis is blocked according to the present embodiments.

After adjustment of the position of the receiving part 1 the rod 12 is inserted and the inner screw 30 is screwed-in between the legs 9, 10 and tightened to exert a pressure onto the rod 12. The rod 12 transmits the pressure to the pressure element, which itself exerts a pressure onto the head 15 to lock it in its final position.

FIGS. 10a and 10b show an outline of alternative embodiments for the pins 33. In the previous embodiments, the pins 33a are shown to have a circular cross-section. The embodiment of FIG. 10a, however, illustrates that the same effect may be achieved using pins 33b having a semi-circular cross-section. As shown in FIG. 10b, a square or rectangular profiled pin 33c, 33e or an elliptical pin 33f, etc. are also possible. Preferred are cylindrical pins for the reason of easier manufacturing. However, flat shapes are also advantageous as these provide a particularly tight contact to the flat surfaces 35a, 35b.

With regard to a semi-circular pin 33d further illustrated in the bottom section of FIG. 10b, the respective through hole may be arranged such that the pins 33d only protrude from the inner surface of the bore 6 or tapered section 7, if the pin 33d is rotated within the bore of the through hole 34. A fixing means (not shown) may be actuated such that this position of the pin 33d within the through hole 34 is retained. An advantage arises as upon spinal surgery the pins may already be inserted prior to applying the anchoring element 13 to the bone. The surgeon merely has to actuate the pin 33d by rotating it within the through hole 34, when a reduction of pivoting movement is desired.

In an alternate embodiment, the fixation element 30 may be composed of an inner member and an outer member (not shown). The outer member is threaded for screwing it into internal thread 11 of the receiving part. A bottom surface of the outer member of the fixation element 30 then exerts a pressure force onto the pressure element 20 in order to fix the head 15. The inner member of the fixation element 30 may be screwed into a threaded bore within the outer member and interacts with the rod 12. It thus becomes possible to fix the rod 12 and the anchoring element 13 separately by means of the two members of the fixation element 30.

According to one embodiment pins may be inserted into through holes formed in the receiving part from outside the receiving part such that the pins cross the spherical portion being used as a bearing for the head of the anchoring element and the pins engage with the recessed surface of the head. Accordingly, the surgeon may fix the degree of rotation depending on the situation. Without the pins, the anchoring element can be pivoted in any direction.

In a modification of the application the receiving part 1 can be used without the pins and with an anchoring element having a spherically shaped head. Hence, the surgeon can decide depending on the actual situation at the operation side whether a monoplanar or a polyaxial anchoring device is to be implanted using one and the same type of receiving part 1.

It is noted that the seat 7 of the receiving part 1 may also be of a conical or any other shape, wherein the same details of construction with regard to the locking device and/or the pins may be applied as described above. Further, the locking device may alternatively be integrally formed with the inner surface of the second bore.

The pins 33 may be inserted into through holes 34, which are oriented within a horizontal plane with regard to the receiving part 1 as shown, e.g., in FIG. 1. However, the invention is not restricted to that specific embodiment. An alternate embodiment shown in FIG. 11 indicates that the through holes 34 may equivalently be arranged in a longitudinal direction with respect to the receiving part 1. The pins 33 are then inserted into the through holes 34 from a bottom side of the receiving part. Other directions of the through holes 34 than horizontal or longitudinal are possible as well.

A further embodiment is shown in FIG. 12. According to this embodiment only one through hole 34 is provided to the receiving part 1. The supply of only one through hole and one pin to be inserted into the through hole may provide sufficient stability when locking the anchoring element 13. In this case, the head 15 of the anchoring element 13 may similarly be provided with only one flat surface 35a (FIG. 12b).

What is claimed is:

1. A bone anchoring device, comprising:
   a receiving part for receiving a rod, the receiving part having a first bore coaxial with a longitudinal axis, a second bore, and a seat comprising an inner wall;
   a pin configured to protrude from a hole recessed inside the inner wall of the seat;
   an anchoring element having a first end configured to attach to a bone and a second end comprising a head configured to be positioned against the seat to engage the pin when the pin is in the hole, the head comprising a surface having a spherically shaped surface portion and an exterior portion from the spherically shaped surface portion;
   wherein the inner wall of the seat is configured to be around the head and to seat the head when the head is positioned in the receiving part;
   wherein pivoting of the anchoring element is limited to a single plane by a connection between the head of the anchoring element and the pin when the head is positioned in the seat and the pin is in the hole;
   wherein the connection comprises a guiding surface of the portion recessed from the spherically shaped surface portion of the head that moves along a guiding surface of the pin resulting in a movement of the anchoring element relative to the receiving part being limited to the single plane; and
   wherein the pin has a first end and a second end at opposite ends of a longitudinal axis of the pin and wherein the first end of the pin and the second end of the pin face away from the head of the anchoring element when the head is positioned in the seat and the pin is in the hole.

2. The bone anchoring device according to claim 1, wherein the hole is a through hole arranged such that upon insertion the pin tangentially engages with the portion recessed from the spherically shaped surface portion of the head.

3. The bone anchoring device according to claim 2, wherein two pins are provided for insertion into respective through holes formed in the receiving part.

4. The bone anchoring device according to claim 2, wherein the through hole extends from a first opening formed in an outer surface of the receiving part towards a second opening formed in the inner wall of the seat, such that the pin protrudes out of the second opening in the inner wall of the seat.

5. The bone anchoring device according to claim 1, wherein the pin is arranged such that the single plane is defined by the longitudinal axis of the receiving part and an axis of the rod when the rod is received in the receiving part.

6. The bone anchoring device according to claim 1, further comprising a pressure element configured to receive the rod, the pressure element configured to be arranged between the head and a fixation element for transmitting pressure to the head in order to lock an angular position of the anchoring element by means of frictional force.

7. The bone anchoring device according to claim 1, wherein the guiding surface of the portion recessed from the spherically shaped surface portion of the head is substantially flat.

8. The bone anchoring device according to claim 1, wherein a fixation element is configured to cooperate with the receiving part to lock the anchoring element relative to the receiving part.

9. A method of anchoring a bone anchoring device to a bone, the method comprising:
- anchoring a bone anchoring assembly to the bone, the bone anchoring assembly comprising a receiving part for receiving a rod and an anchoring element, the receiving part having a first bore coaxial with a longitudinal axis and a second bore, the receiving part comprising a through hole; the anchoring element having a first end for insertion into the bone and a second end positionable within the second bore, the second end comprising a surface having a spherically shaped surface portion and a portion recessed from the spherically shaped surface portion;
- inserting at least one pin in the through hole, the pin protruding from an inner surface of the second bore and moving relative to the portion recessed from the spherically shaped surface portion of the second end of the anchoring element to provide pivoting of the anchoring element relative to the receiving part limited to a single plane;
- inserting a rod in the receiving part;
- adjusting an angular position of the anchoring element relative to the receiving part around a single axis of rotation; and
- inserting a pressure element in the receiving part, the pressure element configured to receive the rod;
- securing the anchoring element relative to the receiving part with a first fixation element transmitting pressure to the second end of the anchoring element in order to lock the angular position of the anchoring element relative to the receiving part by means of frictional force; and
- securing the rod in the pressure element with a second fixation element.

10. A bone anchoring device, comprising:
- a receiving part for receiving a rod, the receiving part having a first bore coaxial with a longitudinal axis, a second bore, and a seat comprising an inner wall;
- a pin configured to protrude from a hole recessed inside the inner wall of the seat;
- an anchoring element having a first end configured to attach to a bone and a second end comprising a head configured to be positioned against the seat to engage the pin when the pin is in the hole, the head comprising a surface having a spherically shaped surface portion and a portion recessed from the spherically shaped surface portion;
- wherein the inner wall of the seat is configured to be around the head and to seat the head when the head is positioned in the receiving part;
- wherein the bone anchoring device is adjustable between a first position, wherein the anchoring element is pivotable in multiple planes when the head is positioned in the seat and the pin is not in the hole and a second position, wherein pivoting of the anchoring element is limited to a single plane by a connection between the head of the anchoring element and the pin when the head is positioned in the seat and the pin is in the hole; and
- wherein the connection comprises a guiding surface of the portion recessed from the spherically shaped surface portion of the head that moves along a guiding surface of the pin resulting in a movement of the anchoring element relative to the receiving part being limited to the single plane.

* * * * *